United States Patent [19]
Okazaki et al.

[11] 4,134,761
[45] Jan. 16, 1979

[54] 3-(9-FLUORENYLIDENE)CARBAZOLE DERIVATIVES AND ELECTROPHOTOGRAPHIC LIGHT-SENSITIVE MATERIAL CONTAINING SAME

[75] Inventors: Mitsuo Okazaki, Tama; Akihiro Yamaguchi, Asaka; Akio Kozima, Yokohama; Masaomi Sasaki, Kawasaki, all of Japan

[73] Assignee: Ricoh Co., Ltd., Tokyo, Japan

[21] Appl. No.: 785,570

[22] Filed: Apr. 7, 1977

[30] Foreign Application Priority Data
Apr. 19, 1976 [JP] Japan .................. 51-44736

[51] Int. Cl.$^2$ .................. G03G 5/04; C07D 209/86
[52] U.S. Cl. .................. 96/1.5 R; 96/1.6; 542/429; 542/448; 542/449
[58] Field of Search .............. 260/315; 96/1.5 C, 1.6, 96/1.5 R; 542/429, 448, 449

[56] References Cited
PUBLICATIONS
Gluzman "Chem. Abstracts" vol. 34 (1940) p. 1314$^2$.

Primary Examiner—Natalie Trousof
Assistant Examiner—R. W. Ramsuer
Attorney, Agent, or Firm—Blanchard, Flynn, Thiel, Boutell & Tanis

[57] ABSTRACT
3-(-fluorenylidene)carbazole derivatives, process for preparing same and electrophotographic light-sensitive material containing 3-(9-fluorenylidene)carbazole derivatives.

4 Claims, 1 Drawing Figure

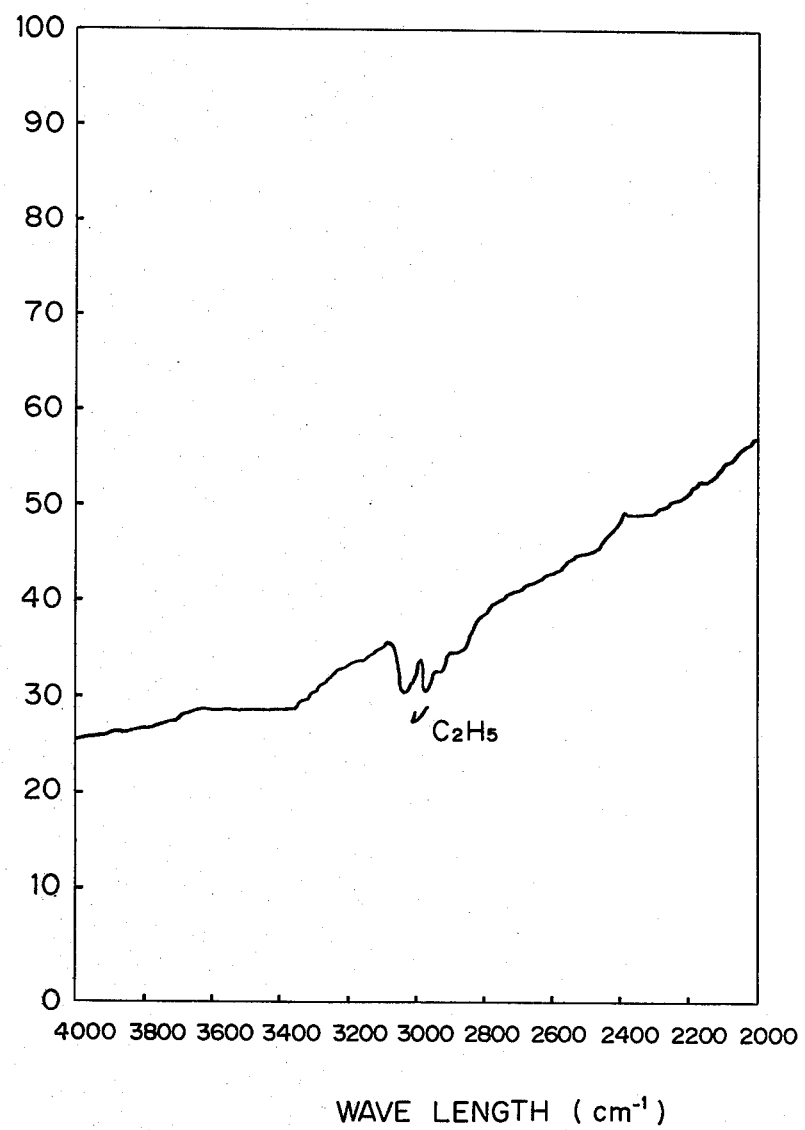

3-(9-FLUORENYLIDENE)CARBAZOLE DERIVATIVES AND ELECTROPHOTOGRAPHIC LIGHT-SENSITIVE MATERIAL CONTAINING SAME

DESCRIPTION OF THE INVENTION

The present invention relates to 3-(9-fluorenylidene)-carbazole derivatives, process for preparing same and electrophotographic light-sensitive materials containing 3-(9-fluorenylidene)carbazole derivative.

Poly-N-vinylcarbazole is well known and is a typical organic photoconductive substance which is used in electrophotographic light-sensitive materials. An object of the present invention is to provide a novel organic photo-conductive substance which is superior to poly-N-vinylcarbazole in the electrophotographic sensitivity.

3-(9-fluorenylidene)carbazole derivatives of the present invention are compounds having the following general formula (I):

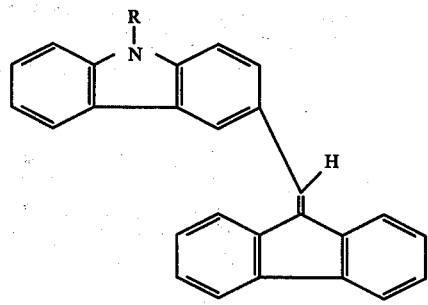

wherein R is a lower alkyl of from 1 to 4 carbon atoms.

Among 3-(9-fluorenylidene)carbazoles of the formula (I), N-ethyl-3-(9-fluorenylidene)carbazole having the following formula (II) is the most useful compound:

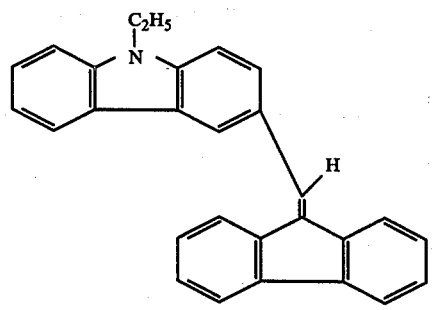

3-(9-fluorenylidene)carbazole derivatives having the general formula (I) can be obtained by reacting a compound of the following formula (III) with a compound of the following formula (IV) or (V) as shown in Processes (A) and (B):

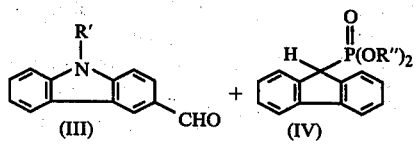

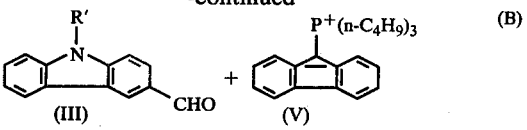

wherein R' and R" are lower alkyl of from 1 to 4 carbon atoms.

In Process (A), carbazole-3-aldehyde of the formula (III) and dialkyl-9-fluorenylphosphonate (IV) are mixed with stirring, at room temperature to 100° C., in the presence of an alkaline catalyst, in an organic solvent. Dialkyl-9-fluorenyl-phosphate of the formula (IV) can be synthesized by the process disclosed in Journal of American Chemical Society, 75, 5892 (1953) by B. E. Smith et al.

Preferred alkaline catalysts include sodium hydroxide, potassium hydroxide, alkoxide of sodium or potassium, sodium hydride, potassium hydride, sodium amide and potassium amide.

Preferred organic solvents include methyl alcohol, ethyl alcohol, iso-propyl alcohol, tert-butyl alcohol, benzene, toluene, xylene, chlorobenzene, dioxane, N,N-dimethylformamide, dimethyl sulfoxide and tetrahydrofuran.

In Process (B), a mixture of carbazole-3-aldehyde of the formula (III) and tri-n-butylphosphonium fluorenylide of the formula (V), in an organic solvent, is heated under reflux for 1 to 4 hours. Tri-n-butylphosphonium fluorenylide of the formula (V) can be synthesized by the process disclosed in Tetrahedron Vol. 9 130 (1960) by A. W. Sohuson. Preferred organic solvents used in this process are benzene, toluene, dichloromethane, carbon tetrachloride and N,N-dimethylformamide.

3-(9-fluorenylidene)carbazole derivatives of the formula (I) have an excellent photoconductive property, so they are used as photoconductive substance for forming a photo-conductive layer of electrophotographic light-sensitive materials. 3-(9-fluorenylidene)carbazole derivatives can be sensitized by addition of optical or chemical sensitizers such as dyes or electron acceptors. Preferred sensitizers include Methyl Violet, Crystal Violet, Methylene Blue and 2,4,7-trinitro-9-fluorenone.

Electrophotographic light-sensitive materials having high quality can be obtained by adding organic pigments or inorganic photoconductive substances to the photoconductive layer comprising 3-(9-fluorenylidene)-carbazole derivatives. Said organic pigments are, for example, metal free phthalocyanine, copper phthalocyanine, Diane Blue (C.I. No. 21180), Indanthrene Red Violet RRN (C.I. No. 73395), indigo, thioindigo, Indanthrene Scarlet R (C.I. No. 71140), and said inorganic photoconductive substances are, for example, zinc oxide, cadmium sulfide and selenium.

Said electrophotographic light-sensitive materials comprising organic pigments or inorganic photoconductive substances and 3-(9-fluorenylidene)carbazole derivatives will be explained as follows:

In recent years, there have been disclosed novel electrophotographic light-sensitive materials comprising charge generating substances and charge transporting substances. For example, in U.S. Pat. Nos. 3,791,826 and 3,837,851, there have been disclosed electrophotographic light-sensitive materials comprising the charge generating substances such as inorganic photoconductive substances and the charge transporting substances such as 2,4,7-trinitro-9-fluorenone or tri-aryl pyrazoline compounds.

The charge generating substances include inorganic photoconductive substances such as Se, Se-Te alloy, Se-Te-As alloy, ZnO, CdS and cadmium sulfoselenide, and organic pigments such as cyanine dye, phthalocyanine, disazo, indigoid, quinacridone, polynuclear quinone, bis-benzimidazole, perylene, methine dye, azo dye, xanthene dye and violantrone.

On the contrary, useful charge transporting substances have not yet been found. 3-(9-fluorenylidene)-carbazole derivatives of the present invention are one of the useful charge transporting substances.

Electrophotographic light-sensitive materials comprising such charge transporting substances can be made by forming a photoconductive layer in a thickness of 3 to 50μ on an electroconductive support, said photoconductive layer comprising a disperse system of 5 to 50% by weight of charge generating substance and 30 to 80% by weight of charge transporting substance in an insulating organic high molecular compound.

The electroconductive support may be a metallic plate such as a plate of aluminum and stainless steel, or a metal-evaporated plastic film. The insulating organic high molecular compound may be polyamide, polyurethane, polyester, epoxy resin, alkyd resin, acrylic resin, silicone resin and cellulose.

Alternatively, the photoconductive layer may be formed in two layers by forming a layer of charge generating substance in thickness of 1μ–5μ on an electroconductive support and then forming a layer of charge transporting substance in thickness of 3 to 50μ on the layer of charge generating substance.

The formation of the photoconductive layer can be effected by coating a dispersion liquid of charge generating substance and/or charge transporting substance in an organic solvent such as toluene or tetrahydrofuran on a support and then drying it.

DESCRIPTION OF THE PREFERRED EMBODIMENTS

The following examples are given by way of illustration only.

EXAMPLE 1.

A solution of 1.5g of metal sodium in 50ml of ethyl alcohol was added to a mixture of 7.1g of N-ethylcarbazole-3-aldehyde (Formula VI) and 10.2g of diethyl-9-fluorenylphosphonate (Formula VII) in 30ml of ethyl alcohol.

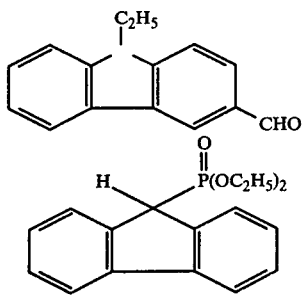

The mixture obtained above was heated under reflux for 30 minutes to obtain a yellowish needle-like crystalline product and further heated for 30 minutes. The crystalline product was filtered off and washed with water, and then dried. A crude product was obtained in a yield of 11.6g (83.8%). A pure crystalline product of N-ethyl-3-(9-fluorenylidene) carbazole (m.p. 171.5–172.0° C.) was obtained by the recrystallization of the crude product from n-butyl alcohol. Analysis:

| Analysis: | C(%) | H(%) | N(%) |
|---|---|---|---|
| Calculated for $C_{27}H_{21}N$ | 90.53 | 5.70 | 3.77 |
| Found | 90.39 | 5.71 | 3.76 |
| Infrared absorption spectrum (KBr tablet method) $\gamma C_2H_5$ $3100-2850 cm^{-1}$ as shown in the accompanying drawing | | | |

Infrared absorption spectrum (KBr tablet method) $\nu C_2H_5$ $3100-2850 cm^{-1}$ as shown in the accompanying drawing.

EXAMPLE 2.

1.3g N-ethylcarbazole-3-aldehyde (Formula VI) and 2.0g tri-n-butylphosphonium fluorenylide (Formula V) was mixed in 40ml of moisture-free benzene. After heating under reflux for 4 hours and then cooling to room temperature, benzene was removed under reduced pressure. A yellowish oily product thus obtained was crystallized by adding n-hexane, and the crystalline product was filtered off and dried. A crude product was obtained in a yield of 2.0g (100%). A pure yellowish needle-like crystalline product of N-ethyl-3-(9-fluorenylidene)carbazole (m.p. 170.5–171.5° C.) was obtained by the recrystallization of the crude product from n-butyl alcohol.

| Analysis: | C(%) | H(%) | N(%) |
|---|---|---|---|
| Calculated for $C_{27}H_{21}N$ | 90.53 | 5.70 | 3.77 |
| Found | 90.50 | 5.69 | 3.78 |
| Infrared absorption spectrum (KBr tablet method) The same data as that in example 1 was obtained. | | | |

Infrared absorption spectrum (KBr tablet method)
The same data as that in Example 1 was obtained.

EXAMPLE 3.

A light-sensitive dispersion liquid containing a photoconductive composition for use in the production of a photoconductive layer was prepared by mixing the following ingredients in a ball mill:

| | |
|---|---|
| N-ethyl-3-(9-fluoroenylidene) carbazole (Formula II) | 10g |
| $H_3CO-\langle\bigcirc\rangle-\overset{OCH_3}{\underset{\underset{+}{O}}{\langle\bigcirc\rangle}}-\langle\bigcirc\rangle-OCH_3 \cdot C_2O_4^-$ | 0.01g |
| polymethyl acrylate | 5g |
| toluene | 100g |

This light-sensitive dispersion liquid was applied as a coat on tracing paper, using a doctor blade, and then dried to obtain an electrophotographic light-sensitive material having a photoconductive layer of about 20μ in thickness formed on the tracing paper.

After the photoconductive layer of the material obtained above was negatively charged by a corona discharge of about −6kV, and then imagewise exposed to a tungsten filament lamp of 20 lux, the material was developed by using a developing liquid (sold by Ricoh Co. under the trade name of BS-1) to obtain a copy having a vivid image. This copy can be used as an intermediate original.

EXAMPLE 4.

2% dispersion liquid of Diane Blue (C.I. No. 21180) in tetrahydrofuran was crushed in a ball mill to obtain a dispersion liquid containing Diane Blue of 1μ in particle size. This dispersion liquid was applied on an aluminum layer on a polyester resin film, using a doctor blade, and then dried to form a layer of 1μ in thickness. Onto this layer was applied, using a doctor blade, a light-sensitive dispersion liquid prepared by mixing the following ingredients, and then dried at a temperature of 100° C. for 30 minutes to obtain an electrophotographic light-sensitive material having a photoconductive layer of about 15μ in thickness.

| | |
|---|---|
| N-ethyl-3-(9-fluoroenylidene) carbazole (Formula (II) | 1 g |
| polycarbonate (sold by K.K. Taijin under the trademark Panlite L-1250) | 1 g |
| tetrahydrofuran | 100 ml |

The electroconductive layer of the light-sensitive material obtained above was negatively charged by a corona discharge of about −6kV to obtain a surface electric potential, and then the charged material was exposed to a tungsten filament lamp whose illuminance at the surface of the light-sensitive layer was adjusted to be 20 lux. The time (seconds) required to reduce the surface electric potential to one half of the initial surface potential was measured. The amounts of exposure required to reduce the surface electric potential to one half ($E_{1/2}$) are calculated by "20 lux X time (second)". The amounts of exposure ($E_{1/2}$) was 4 lux.sec.

Another light-sensitive material obtained above was negatively charged as shown above and imagewise exposed to a tungsten filament lamp as shown in Example 3 to form an electrostatic latent image on the photoconductive layer, and then developed by using positively charged toners in dry form to produce a toner image on the material. By electrostatically transferring the toner image to paper, a vivid positive-to-positive copy was obtained. In the development, toners in wet form can be used instead of toners in dry form.

EXAMPLE 5

A light-sensitive dispersion liquid was prepared by mixing the following ingredients in a ball mill:

| | |
|---|---|
| N-ethyl-3-(9-fluorenylidene) carbazole (Formula II) | 1 g |
| polyester resin (sold by E.I. Du Pont de Nemours & Co., Inc. under the trademark of Polyester Adhesive 49000) | 1 g |
| tetrahydrofuran | 100 ml |
| β-type copper phthalocyanine (sold by Sumitomo Chemical Co., Ltd. under the trademark of Sumitomo Cyanine Blue LBG) | 0.1 g |

This light-sensitive dispersion liquid was applied on an aluminum layer on a polyester resin film, using a doctor blade, and then dried at a temperature of 100° C. for 30 minutes to obtain an electrophotographic light-sensitive material having a photoconductive layer of about 20μ in thickness on the aluminum film.

The electroconductive layer of the light-sensitive material obtained above was positively charged by a corona discharge of about +6kV to obtain a surface electric potential, and then the charged material was exposed to a tungsten filament lamp as shown in Example 4. The amount exposure ($E_{1/2}$) was 4.5 lux.sec.

Another light-sensitive material obtained above was positively charged as shown above and imagewise exposed to a tungsten filament lamp as shown in Example 3, and then developed by using negatively charged toners in dry or wet form to produce a toner image on the material. By electrostatically transferring the toner image to paper, a vivid positive-to-positive copy was obtained by using the toners in dry or wet form.

We claim:

1. 3-(9-fluorenylidene)carbazole derivatives having the formula (I):

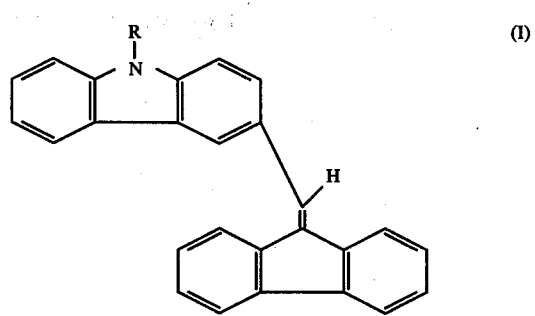

wherein R is a lower alkyl group of from 1 to 4 carbon atoms.

2. 3-(9-fluorenylidene)carbazole derivative according to claim 1 wherein said derivative has the formula (II):

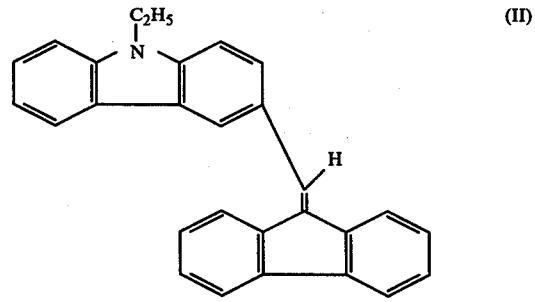

3. An electrophotographic light-sensitive material comprising an electrically conductive support, a photoconductive layer on said electrically conductive support, said photoconductive layer having a thickness of 3 to 50μ, said photoconductive layer consisting essentially of from 30 to 80% by weight of a charge transport compound having the formula

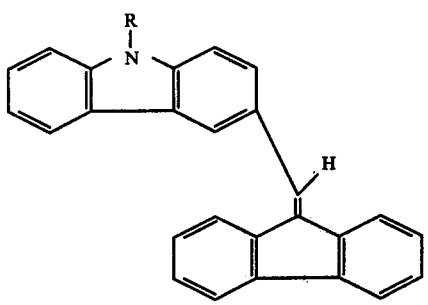
(I)

wherein R is alkyl having 1 to 4 carbon atoms, from 5 to 50% by weight of charge generating substance selected from the group consisting of cyanine dye, phthalocyanine, disazo, indigoid, quinacridone, polynuclear quinone, bis-benzimidazole, perylene, methine dye, azo dye, xanthene dye and violanthrone, and the balance is an insulating organic high molecular weight compound.

4. An electrophotographic light-sensitive material comprising an electrically conductive support, a first layer on said support, said first layer having a thickness of from 1 to $5\mu$ and consisting essentially of charge generating substance selected from the group consisting of Se, Se-Te alloy, Se-Te-As alloy, Zno, CdS, cadmium sulfoselenide, cyanine dye, phthalocyanine, disazo, indigoid, quinacridone, polynuclear quinone, bis-benzimidazole, perylene, methine dye, azo dye, xanthene dye and violanthrone, and a charge transport layer on said first layer, said charge transport layer having a thickness of from 3 to $50\mu$ and consisting essentially of a charge transport substance and an insulating organic high molecular compound, said charge transport substance having the formula

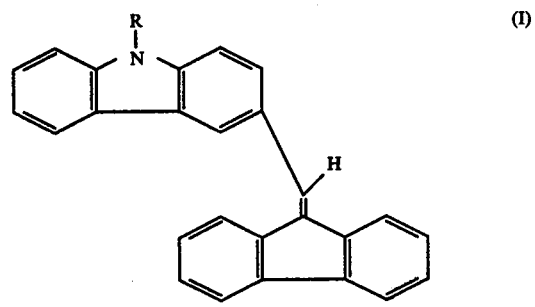
(I)

wherein R is alkyl having 1 to 4 carbon atoms.

* * * * *